US008765390B2

(12) United States Patent
Ailles et al.

(10) Patent No.: US 8,765,390 B2
(45) Date of Patent: Jul. 1, 2014

(54) IDENTIFICATION AND ISOLATION OF SQUAMOUS CARCINOMA STEM CELLS

(75) Inventors: Laurie Ailles, Palo Alto, CA (US); Irving L. Weissman, Stanford, CA (US); Michael Clarke, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 431 days.

(21) Appl. No.: 12/001,336

(22) Filed: Dec. 10, 2007

(65) Prior Publication Data

US 2008/0220453 A1 Sep. 11, 2008

Related U.S. Application Data

(60) Provisional application No. 60/873,765, filed on Dec. 8, 2006.

(51) Int. Cl.
*G01N 33/574* (2006.01)
*G01N 33/483* (2006.01)

(52) U.S. Cl.
USPC .......................................... 435/7.23; 435/40.52

(58) Field of Classification Search
None
See application file for complete search history.

(56) References Cited

U.S. PATENT DOCUMENTS 7,115,360 B2 * 10/2006 Clarke et al. ...................... 435/4
2008/0064049 A1 * 3/2008 Clarke et al. ................. 435/7.23

OTHER PUBLICATIONS

Tockman et al (Cancer Res., 1992, 52:2711s-2718s).*
Jensen et al (Cancer letters, 2008, 272:23-31, internet pp. 1-14).*
Loebinger et al (British J of Cancer, 2008, 98:380-387).*
Prince et al (Proceedings of the American Assoc Cancer Res, AACR Meeting Abstract, Apr. 2006, vol. 47:938, abstract #3983, 2 pages).*
Song et al (Cancer Research, Jun. 2006, 66:6225-6232).*
Lindberg et al (American J Pathology, 1989, 134:89-98).*
Al-Hajj et al., "Prospective identification of tumorigenic breast cancer cells," Proc. Natl. Acad. Sci. USA, 2003, 100 (7):3983-3988.
Lessard et al., "Bmi-1 determines the proliferative capacity of normal and leukaemic stem cells," Nature, 2003, 423 (6937):255-260.
Li et al., "Identification of pancreatic cancer stem cells," Cancer Res., 2007, 67(3):1030-1037.
Molofsky et al., "Bmi-1 dependence distinguishes neural stem cell self-renewal from progenitor proliferation," Nature, 2003, 425(6961):962-967.
O'Brien et al., "A human colon cancer cell capable of initiating tumour growth in immunodeficient mice," Nature, 2007, 445(7123):106-110.
Pardal et al., "Applying the principles of stem-cell biology to cancer," Nat. Rev. Cancer, 2003, 3(12):895-902.
Park et al., "Bmi-1 is required for maintenance of adult self-renewing haematopoietic stem cells," Nature, 2003, 423 (6937):302-305.
Park et al., "Bmi1, stem cells, and senescence regulation," J Clin. Invest., 2004, 113(2):175-179.
Phillips et al., "The response of CD24(-/low)/CD44+ breast cancer-initiating cells to radiation," J Natl. Cancer Inst., 2006, 98(24):1777-1785.
Reya et al., "Stem cells, cancer, and cancer stem cells," Nature, 2001, 414(6859):105-111.
Ricci-Vitiani et al., "Identification and expansion of human colon-cancer-initiating cells," 2007, Nature, 445 (7123):111-115.
Valk-Lingbeek et al., "Stem cells and cancer; the polycomb connection," Cell, 2004, 118(4):409-418.

* cited by examiner

*Primary Examiner* — Laura B Goddard
(74) *Attorney, Agent, or Firm* — Bozicevic, Field & Francis LLP; Pamela J. Sherwood

(57) ABSTRACT

Squamous carcinoma stem cells (SCSC) are identified. The cells can be prospectively isolated or identified from primary tumor samples, and are shown to possess the unique properties of cancer stem cells in functional assays for cancer stem cell self-renewal and differentiation, and to form unique histological microdomains useful in cancer diagnosis.

8 Claims, 5 Drawing Sheets
(5 of 5 Drawing Sheet(s) Filed in Color)

Primary tumor
First passage
Second Passage
UMHN2
SUHN1
Transplant CD44+ cells
Transplant CD44+ cells
Transplant CD44+ cells
Transplant CD44+ cells
CD44

IDENTIFICATION AND ISOLATION OF SQUAMOUS CARCINOMA STEM CELLS

FEDERALLY-SPONSORED RESEARCH OR DEVELOPMENT

This invention was made with Government support under contract CA104987 awarded by the National Institutes of Health. The Government has certain rights in this invention.

BACKGROUND OF THE INVENTION

Basic cancer research has focused on identifying the genetic changes that lead to cancer. This has led to major advances in our understanding of the molecular and biochemical pathways that are involved in tumorigenesis and malignant transformation. However, our understanding of the cellular biology has lagged. Although the effects of particular mutations on the proliferation and survival of model cells, such as fibroblasts or cell lines, can be predicted, the effects of such mutations on the actual cells involved in specific cancers is largely guesswork.

A tumor can be viewed as an aberrant organ initiated by a tumorigenic cancer cell that acquired the capacity for indefinite proliferation through accumulated mutations. In this view of a tumor as an abnormal organ, the principles of normal stem cell biology can be applied to better understand how tumors develop. Many observations suggest that analogies between normal stem cells and tumorigenic cells are appropriate. Both normal stem cells and tumorigenic cells have extensive proliferative potential and the ability to give rise to new (normal or abnormal) tissues. Both tumors and normal tissues are composed of heterogeneous combinations of cells, with different phenotypic characteristics and different proliferative potentials.

Because most tumors have a clonal origin, the original tumorigenic cancer cell gives rise to phenotypically diverse progeny, including cancer cells with indefinite proliferative potential, as well as cancer cells with limited or no proliferative potential. This suggests that tumorigenic cancer cells undergo processes that are analogous to the self-renewal and differentiation of normal stem cells. Tumorigenic cells can be thought of as cancer stem cells that undergo an aberrant and poorly regulated process of organogenesis analogous to what normal stem cells do. Although some of the heterogeneity in tumors arises as a result of continuing mutagenesis, it is likely that heterogeneity also arises through the aberrant differentiation of cancer cells.

It is well documented that many types of tumors contain cancer cells with heterogeneous, phenotypes, reflecting aspects of the differentiation that normally occurs in the tissues from which the tumors arise. The variable expression of normal differentiation markers by cancer cells in a tumor suggests that some of the heterogeneity in tumors arises as a result of: the anomalous differentiation of tumor cells. Examples of this include the variable expression of myeloid markers, in chronic myeloid leukaemia, the variable expression of neuronal markers, within peripheral neurectodermal tumors, and the variable expression of milk proteins or the oestrogen receptor within breast cancer.

It was first extensively documented for leukaemia and multiple myeloma that only a small subset of cancer cells is capable of extensive proliferation. Because the differences in clonogenicity among the leukemia cells mirrored the differences in clonogenicity among normal hematopoietic cells, the clonogenic leukemic cells were described as leukemic stem cells. It has also been shown for solid cancers that the cells are phenotypically heterogeneous and that only a small proportion of cells are clonogenic in culture and in vivo. Just as in the context of leukemic stem cells, these observations led to the hypothesis that only a few cancer cells are actually tumorigenic and that these tumorigenic cells act as cancer stem cells.

In support of this hypothesis, recent studies have shown that, similar to leukemia and other hematologic malignancies, tumorigenic and non-tumorigenic populations of breast cancer cells can be isolated based on their expression of cell surface markers. In many cases of breast cancer, only a small subpopulation of cells had the ability to form new tumors. This work strongly supports the existence of CSC in breast cancer. Further evidence for the existence of cancer stem cells occurring in solid tumors has been found in central nervous system (CNS) malignancies. Using culture techniques similar to those used to culture normal neuronal stem cells it has been shown that neuronal CNS malignancies contain a small population of cancer cells that are clonogenic in vitro and initiate tumors in vivo, while the remaining cells in the tumor do not have these properties.

Stem cells are defined as cells that have the ability to perpetuate themselves through self-renewal and to generate mature cells of a particular tissue through differentiation. In most tissues, stem cells are rare. As a result, stem cells must be identified prospectively and purified carefully in order to study their properties. Perhaps the most important and useful property of stem cells is that of self-renewal. Through this property, striking parallels can be found between stem cells and cancer cells: tumors may often originate from the transformation of normal stem cells, similar signaling pathways may regulate self-renewal in stem cells and cancer cells, and cancers may comprise rare cells with indefinite potential for self-renewal that drive tumorigenesis.

The presence of cancer stem cells has profound implications for cancer therapy. At present, all of the phenotypically diverse cancer cells in a tumor are treated as though they have unlimited proliferative potential and can acquire the ability to metastasize. For many years, however, it has been recognized that small numbers of, disseminated cancer cells can be detected at sites distant from primary tumors in patients that never manifest metastatic disease. One possibility is that immune surveillance is highly effective at killing disseminated cancer cells before they can form a detectable tumor. Another possibility is that most cancer cells lack the ability to form a new tumor such, that only the dissemination of rare cancer stem cells can lead to metastatic disease. If so, the goal of therapy must be to identify and kill this cancer stem cell population.

The prospective identification and isolation of cancer stem cells will allow more efficient identification of diagnostic markers and therapeutic targets expressed by the stem cells. Existing therapies have been developed largely against the bulk population of tumor cells, because the therapies are identified by their ability to shrink the tumor mass. However, because most cells within a cancer have limited proliferative potential, an ability to shrink a tumor mainly reflects an ability to kill these cells. Therapies that are more specifically directed against cancer stem cells may result in more durable responses and cures of metastatic tumors.

Epithelial tumors, including head and neck squamous cell carcinoma (HNSCC), contain a mixed population of cancer cells. It has been hypothesized that functional heterogeneity rather than cellular heterogeneity may account for the fact that not all of the cancer cells in solid tumors have a similar ability to drive tumor formation. Head and neck cancer is a common malignancy that affects approximately 40,000 new patients in the United States each year. Despite advances in therapy, which have improved quality of life, survival rates have remained static for many years. Mortality from this disease remains high due to the development of distant metastasis and the emergence of therapy resistant local and regional recurrences. It is therefore essential that we develop a deeper understanding of the biology of this disease in order to develop more effective therapies.

References of interest include, without limitation, a discussion of BM1 by Lessard, & Sauvageau (2003) *Nature* 423, 255-60; Molofsky et al. (2003) *Nature* 425, 962-7; Park et al. (2004) *J Clin Invest* 113, 175-9; Park et al. (2003) *Nature* 423, 302-5; and Valk-Lingbeek, M. E., Bruggeman, S. W. & van Lohuizen, M. (2004) *Cell* 118, 409-18.

Cancer Stem cells are discussed in, for example, Pardal et al. (2003) Nat Rev Cancer 3, 895-902; Reya et al. (2001) Nature 414, 105-11; Bonnet & Dick (1997) Nat Med 3, 730-7; Al-Hajj et al. (2003) Proc Natl Acad Sci USA 100, 3983-8; Dontu et al. (2004) Breast Cancer Res 6, R605-15; Singh et al. (2004) Nature 432, 396-401.

SUMMARY OF THE INVENTION

Squamous carcinoma stem cells (SCSC) are identified herein. The cells can be prospectively isolated or identified from primary tumor samples, and are shown to possess the unique properties of cancer stem cells in functional assays for cancer stem cell self-renewal and differentiation, and to form unique histological microdomains useful in cancer diagnosis. The SCSC have the phenotype of being positive for expression of CD44, and negative for expression of specific lineage markers. The SCSC are further shown to differentially express the Bmi1 gene, both at the RNA and protein levels. The CD44+ cells in the tumor express high levels of nuclear Bmi1.

In some embodiments of the invention, methods are provided for classification or clinical staging of squamous cell carcinomas according to the stem cells that are present in the carcinoma, where greater numbers of stem cells are indicative of a more aggressive cancer phenotype. Staging is useful for prognosis and treatment. In some embodiments, a tumor sample is analyzed by histochemistry, including immunohistochemistry, in situ hybridization, and the like, for the presence of cells that co-express CD44 at the cell membrane and Bmi1 in the nucleus. The presence of such cells indicates the presence of SCSC, and allows the definition of cancer stem cell microdomains in the primary tumor, as well as cells in lymph node or distant metastases.

In another embodiment of the invention, compositions of isolated SCSC are provided. The cells are useful for experimental evaluation, and as a source of lineage and cell specific products, including mRNA species useful in identifying genes specifically expressed in these cells, and as targets for the discovery of factors or molecules that can affect them. SCSC may be used, for example, in a method of screening a compound for an effect on the cells. This involves combining the compound with the cell population of the invention, and then determining any modulatory effect resulting from the compound. This may include examination of the cells for viability, toxicity, metabolic change, or an effect on cell function. The phenotype of SCSC described herein provides a means of predicting disease progression, relapse, and development of drug resistance.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
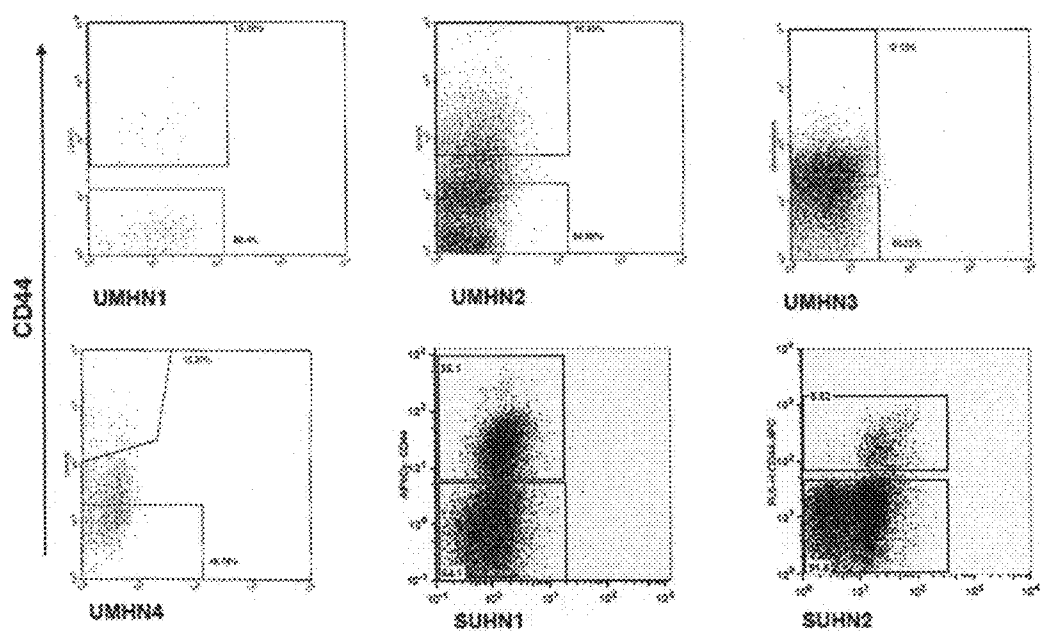
FIG. 1. Isolation of tumorigenic cells for specimens UMHN1-7 and SUHN1-2. Flow cytometry was used to isolate subpopulations of cells based on their CD44 expression. Dead cells (7AAD+ or PI+) and Lineage+ cells were eliminated from all analyses. CD44 is shown on the y axis, versus an empty channel on the x axis. Each plot depicts the CD44 staining pattern of live, Lineage− human HNSCC cells, and the frequency of the boxed tumorigenic cancer cell population as a percentage of the cancer cells is shown.

Squamous cell carcinomas are staged by analysis of the presence of cancer stem cells. Staging is useful for prognosis and treatment. In one embodiment of the invention, a biopsy sample from a squamous carcinoma patient is stained with reagents specific for CD44; optionally a lineage panel. Staining reagents may further include reagents specific for cytokeratin 5/14, which the SCSC express. The analysis of staining patterns lineage negative, CD44+ compartment provides the relative distribution of SCSC, which distribution predicts the stage of carcinoma. In some embodiments, the biopsy sample is analyzed by histochemistry, including immunohistochemistry, in situ hybridization, and the like, for the presence of cells that co-express CD44 at the cell membrane and Bmi1 in the nucleus. The presence of such cells indicates the presence of SCSC, and allows the definition of cancer stem cell microdomains in the primary tumor, as well as cells in lymph node or distant metastases.

In one embodiment, the patient sample is compared to a control, or a standard test value. In another embodiment, the patient sample is compared to a pre-carcinoma sample, or to one or more time points through the course of the disease.

Samples, including tissue sections, slides, etc. containing a squamous carcinoma tissue, are stained with reagents specific for markers that indicate the presence of cancer stem cells. Samples may be frozen, embedded, present in a tissue microarray, and the like. The reagents, e.g. antibodies, polynucleotide probes, etc. may be detectably labeled, or may be indirectly labeled in the staining procedure. The data provided herein demonstrate that the number and distribution of progenitor cells is diagnostic of the stage of the carcinoma.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example; genetic abnormalities can be causative of disease susceptibility or drug responsiveness, or can be linked to such phenotypes.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims. In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

As summarized above, the subject invention is directed to methods of classification of cancers, as well as reagents and kits for use in practicing the subject methods. The methods may also determine an appropriate level of treatment for a particular cancer.

Methods are also provided for optimizing therapy, by first classification, and based on that information, selecting the appropriate therapy, dose, treatment modality, etc. which optimizes the differential between delivery of an anti-proliferative treatment to the undesirable target cells, while minimizing undesirable toxicity. The treatment is optimized by selection for a treatment that minimizes undesirable toxicity, while providing for effective anti-proliferative activity.

The invention finds use in the prevention, treatment, detection or research squamous cell carcinomas. Carcinomas are malignancies that originate in the epithelial tissues. Epithelial cells cover the external surface of the body, line the internal cavities, and form the lining of glandular tissues. In adults, carcinomas are the most common forms of cancer.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

The term "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "individual," "subject," "host," and "patient," used interchangeably herein and refer to any mammalian subject for whom diagnosis, treatment, or therapy is desired, particularly humans. Other subjects may include cattle, dogs, cats, guinea pigs, rabbits, rats, mice, horses, and the like.

A "host cell", as used herein, refers to a microorganism or a eukaryotic cell or cell line cultured as a unicellular entity which can be, or has been, used as a recipient for a recombinant vector or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

The term "normal" as used in the context of "normal cell," is meant to refer to a cell of an untransformed phenotype or exhibiting a morphology of a non-transformed cell of the tissue type being examined.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

"Therapeutic target" generally refers to a gene or gene product that, upon modulation of its activity (e.g., by modulation of expression, biological activity, and the like), can provide for modulation of the cancerous phenotype.

As used throughout, "modulation" is meant to refer to an increase or a decrease in the indicated phenomenon (e.g., modulation of a biological activity refers to an increase in a biological activity or a decrease in a biological activity).

Characterization of Squamous Carcinoma Stem Cells

In squamous cell carcinomas, characterization of cancer stem cells allows for the development of new treatments that are specifically targeted against this critical population of cells, particularly their ability to self-renew, resulting in more effective therapies. "Squamous cell carcinomas", as used herein, refers to the epithelial tumors found in many in many different organs, including the skin, mouth, esophagus, lungs, and cervix, which show squamous cell differentiation. Included are head and neck squamous cell carcinomas, lung squamous cell carcinomas, skin squamous cell carcinomas, otic squamous cell carcinomas, vulval squamous cell carcinomas, cervical squamous cell carcinomas, esophageal squamous cell carcinomas, and the like. In some embodiments, the squamous cell carcinoma is a head and neck squamous cell carcinoma.

In human squamous cell carcinomas it is shown herein that there is a subpopulation of tumorigenic cancer cells with both self-renewal and differentiation capacity. These tumorigenic cells are responsible for tumor maintenance, and also give rise to large numbers of abnormally differentiating progeny that are not tumorigenic, thus meeting the criteria of cancer stem cells. All tumorigenic potential was contained within the CD44+ Lineage− subpopulation of cancer cells. These cells were able to initiate tumor growth at a dose of from about 1 cells, about $5\times10^3$ cells, about $10^4$ cells, in comparison to while tumor suspension, which required a dose of around about $10^6$ cells to form a tumor, and a lack of tumor formation by CD44− Lineage− cells at much higher cell doses.

The SCSC are identified by their phenotype with respect to particular markers, and/or by their functional phenotype. In some embodiments, the SCSC are identified and/or isolated by binding to the cell with reagents specific for the markers of interest. The cells to be analyzed may be viable cells, or may be fixed or embedded cells.

In some embodiments, the reagents specific for the markers of interest are antibodies, which may be directly or indirectly labeled. Such antibodies will usually include antibodies specific for CD44; and antibodies specific for a lineage panel. The lineage panel will usually include reagents specific for markers of normal leukocytes, fibroblasts, endothelial, mesothelial cells, etc. Such markers may include reagents specific for one or more, two or more, three or more of the following markers: CD45; CD31; CD140; CD2, CD3, CD10, CD18, CD31, CD64 and Q140b. In some embodiments the lineage panel comprises CD45; CD31; and CD140 specific reagents. In other embodiments, the lineage panel comprises CD2, CD3, CD10, CD18, CD31, CD64 and Q140b specific reagents.

Reagents of interest for identification and/or isolation of SCSC may further include reagents specific for Cytokeratin 5/14 (CK5/14), a basal layer marker, or with an antibody to Involucrin, a differentiated keratinocyte marker. The SCSC express CK5/14, and lack expression of Involucrin.

The SCSC differentially expresses Bmi1, and may be stained with antibodies specific for the Bmi1 protein, or identified with genetic probes specific for the Bmi1 mRNA, e.g. in situ hybridization, etc. The human Bmi1 gene is described, for example, in Alkema et al. (1993) Hum. Mol. Genet. 2(10): 1597-1603, and is deposited in Genbank, accession number L13689. The protein encoded by the BMI1 gene has a domain of homology to a Drosophila protein encoded by a member of the Polycomb-group gene family, which is required to maintain the repression of homeotic genes. The fact that mice lacking the BMI1 gene showed posterior transformations of the axial skeleton BMI1 appears to be a member of a vertebrate Polycomb complex that regulates segmental identity by repressing HOX genes throughout development. In the mouse, Bmi1 is required for the self-renewal of stem cells in the peripheral and central; nervous systems but not for their survival or differentiation. The reduced self-renewal of Bmi1-deficient neural stem cells led to their postnatal depletion. It has been proposed that BMI1 dependence distinguishes stem cell self-renewal from restricted progenitor proliferation in certain tissues. The combination of CD44 positive staining at the cell membrane and Bmi1 staining in the nucleus allows the definition of cancer stem cell microdomains in the primary tumor. The presence of such microdomains is useful in diagnosis of squamous cell carcinoma in primary and metastatic sites, where increased numbers of such microdomains is indicative of tumors with a greater capacity for tumorigenesis.

Upon reanalysis of tumors arising from the transplantation of purified CD44+ cells, both CD44+ and CD44− cells were again present, indicating that tumorigenic CD44+ cells give rise to nontumorigenic CD44− cells. Furthermore, serial transplants demonstrate that with each tumor passage, only CD44+Lineage− and not the CD44− Lineage− cells can initiate a new tumor. Each time, the tumor again contains a mixture of CD44+ and CD44− cells. Over multiple transplants, a large expansion of the CD44+ population occurs that can only be accounted for by self-renewal of the tumorigenic population. Self-renewal is a hallmark property of stem cells.

Further evidence for a developmental hierarchy in HNSCC comes from the histology and immunohistochemistry studies done on moderate-to-well differentiated tumors. The tumors demonstrate cytologic and architectural features similar to normal squamous epithelium, including differentiation from a basal layer towards an apical layer containing cells with mature squamous morphology, and the formation of keratin (keratin pearls were present). CD44 clearly stains regions of the tumors that have basal cell morphology and that costain with the basal layer marker CK5/14. Finally, the differentiation marker Involucrin stains the regions of the tumor that are negative for CD44, and vice versa.

In squamous cell carcinomas, a subpopulation of cells possess the properties of cancer stem cells. These cells form tumors in vivo; self-renew to generate tumorigenic progeny; give rise to abnormally differentiated, nontumorigenic progeny, and differentially express at least one stem cell-associated gene. This population can be enriched by selecting for cells that express the cell surface marker CD44.

Squamous Cell Carcinomas

Squamous cells are flat cells which form the surface of an epithelium. They can be identified histologically by the fact that they look flattened and thin under a microscope. Epithelia lined by squamous cells can be classified as either simple squamous epithelium or stratified squamous epithelium.

Squamous cell carcinoma is a carcinoma that may occur in many different organs, including the skin, mouth, esophagus, lungs, and cervix. It, is a malignant tumor of epithelium that shows squamous cell differentiation. Squamous cell carcinoma is usually developed in the epithelial layer of the skin and sometimes in various mucous membranes of the body. This type of cancer can be seen on the skin, lips, inside the mouth, throat or esophagus.

The most common noncutaneous tumor of the head and neck is squamous cell carcinoma of the larynx, followed by squamous cell carcinomas of the palatine tonsil, tongue, and floor of the mouth. Somewhat less common are tumors of the salivary gland, jaw, nose and paranasal sinuses, and ear. Tumors of the thyroid gland, eye, and skin are discussed elsewhere in the manual. Excluding the skin and thyroid gland, >90% of head and neck cancers are squamous cell (epidermoid) carcinomas, and 5% are melanomas, lymphomas, and sarcomas. The Epstein-Barr virus plays a role in the pathogenesis of nasopharyngeal cancer.

Most head and neck cancers first manifest as an asymptomatic lump, ulceration, or visible mucosal lesion (eg, leukoplakia, erythroplakia). Subsequent symptoms depend on location and extent of the tumor and include pain, paresthesia, nerve palsies, trismus, and halitosis. Head and neck cancers may remain localized for months to years. Local tissue invasion is eventually followed by metastasis to regional lymph nodes. Distant lymphatic metastases tend to occur late. Hematogenous metastases are usually associated with large or persistent tumors and occur more commonly in immunocompromised patients. Common sites of distant metastases are the lungs, liver, bone, and brain.

Prognosis is favorable if diagnosis is early and treatment is timely and appropriate. Exophytic or verrucous tumors generally respond better than do invasive, infiltrative, or ulcerative tumors. In general, the more poorly differentiated the cancer, the greater the chance of regional and distant metastases. With invasion of muscle, bone, or cartilage, cure rates are significantly decreased. Perineural spread, as evidenced by pain, paralysis, or numbness, indicates a highly aggressive tumor that is unlikely to be cured. Cervical or distant metastasis greatly reduces survival rate. With appropriate treatment, 5-yr survival approaches 90% for stage I, 75% for stage II, 45 to 75% for stage III, and <35% for stage IV. Patients>70 yr often have longer disease-free intervals and better survival rates.

Oral squamous cell carcinoma affects about 30,000 Americans each year. Oral squamous cell carcinoma is the most common oral or pharyngeal cancer. The chief risk factors for oral squamous cell carcinoma are smoking and alcohol use. Squamous cell carcinoma of the tongue may also result, from Plummer-Vinson syndrome, syphilis, or chronic trauma. About 40% of intraoral squamous cell carcinomas begin on the floor of the mouth or on the lateral and ventral surfaces of the tongue. About 38% of all oral squamous cell carcinomas occur on the lower lip, and about 11% begin in the palate and tonsillar area.

Oral lesions are asymptomatic initially. They may appear in areas of erythroplakia or leukoplakia and may be exophytic or ulcerated. Both variants are indurated and firm with a rolled border. Tonsillar carcinoma usually presents as an asymmetric swelling and sore throat; pain often radiates to the ipsilateral ear. A metastatic mass in the neck may be the first symptom.

If carcinoma of the tongue is localized (no lymph node involvement), 5-yr survival is about 50%. For localized carcinoma of the floor of the mouth, 5-yr survival is 65%. With lymph node metastasis, the 5-yr survival is 20%. For lower lip lesions, 5-yr survival is 90%, and metastases are rare. Carcinoma of the upper lip tends to be more aggressive and metastatic. For carcinoma of the palate and tonsillar area, 5-yr survival is 68% if patients are treated before lymph node involvement but only 17% after involvement. Metastases reach the regional lymph nodes first and later the lungs. Surgery and radiation therapy are the treatments of choice.

About 90% of vulvar cancers are squamous cell carcinomas; about 5% are melanomas. Vulvar cancer most often occurs in elderly women. It usually manifests as a palpable lesion. Diagnosis is by biopsy. Treatment includes excision and inguinal and femoral lymph node dissection. Vulvar cancer accounts for about 3 to 4% of gynecologic cancers in the US. Average age at diagnosis is about 70, and incidence increases with age. Risk factors include vulvar intraepithelial neoplasia (VIN), human papillomavirus infection, heavy cigarette smoking, lichen sclerosis, squamous hyperplasia, squamous carcinoma of vagina or cervix, and chronic granulomatous diseases. VIN is a precursor to vulvar cancer. VIN may be multifocal. Sometimes adenocarcinoma of the vulva, breast, or Bartholin's glands also develops.

The most common presentation is a palpable vulvar lesion, frequently noticed by the woman or by a clinician during pelvic examination. Overall 5-yr survival rates are >90% with stage I, 80% with stage II, 50 to 60% with stage III, and 15% with stage IV. Risk of lymph node spread is proportional to the tumor size and invasion depth.

Squamous cell carcinoma of the skin is a malignant tumor of epidermal keratinocytes that invades the dermis, usually occurring in sun-exposed areas. The incidence in the US is 80,000 to 100,000 cases annually, with 2000 deaths. Local destruction may be extensive, and metastases occur in advanced stages. Diagnosis is by biopsy. Treatment depends on the tumor's characteristics and may involve curettage and electrodesiccation, surgical excision, cryosurgery, or, occasionally, radiation therapy.

The clinical appearance is highly variable, but any nonhealing lesion on sun-exposed surfaces should be suspect. The tumor may begin as a red papule or plaque with a scaly or crusted surface and may become nodular, sometimes with a warty surface. In some, the bulk of the lesion may lie below the level of the surrounding skin. Eventually the tumor ulcerates and invades the underlying tissue. The percentage of squamous cell carcinomas on sun-exposed skin that metastasize is quite low. However, about ⅓ of lingual or mucosal cancers have metastasized before diagnosis.

In general, the prognosis for small lesions removed early and adequately is excellent. Regional and distant metastases are uncommon but do occur, particularly with poorly differentiated tumors. Late-stage disease may require extensive surgery and is far more likely to metastasize, initially locoregionally to surrounding skin and lymph nodes and eventually to nearby organs. The overall 5-yr survival rate for metastatic disease is 34% despite therapy. Treatment is the same as for basal cell carcinoma, but treatment and follow-up must be monitored closely because of the greater risk of metastasis.

Squamous cell carcinoma is the most common malignancy of the larynx. In the US, it is 4 times more common in men and is more common among blacks than whites. Over 95% of patients are smokers; 15 pack-years of smoking increases the risk 30-fold. Sixty percent of patients present with localized disease alone, 25% with local disease and regional nodal metastatic disease, and 15% with advanced disease, distant metastases, or both. Common sites of origin are the true vocal cords (glottis) particularly the anterior portion, supraglottic larynx (epiglottis), hypopharynx (pyriform sinus), and post-cricoid area.

For early-stage glottic carcinoma, laser excision, radiation therapy, or sometimes cordectomy results in a 5-yr survival rate of 85 to 95%; laser excision and radiation therapy usually preserve a normal voice. For advanced carcinoma with anterior commissure involvement, impaired vocal cord mobility, thyroid cartilage invasion, or subglottic extension, surgery is necessary.

The most common malignant esophageal tumor is squamous cell carcinoma. Symptoms are progressive dysphagia and weight loss. Diagnosis is by endoscopy, followed by CT and endoscopic ultrasound for staging. Treatment varies with stage and generally includes surgery with or without chemotherapy and radiation. Long-term survival is poor except for those with local disease. About 8000 cases of esophageal squamous cell carcinoma occur annually in the US.

Early-stage esophageal cancer tends to be asymptomatic. When the lumen of the esophagus becomes constricted to <14 mm, dysphagia commonly occurs. Lymphatic spread to internal jugular, cervical, supraclavicular, mediastinal, and celiac nodes is common. The tumor usually metastasizes to lung and liver and occasionally to distant sites (eg, bone, heart, brain, adrenal glands, kidneys, peritoneum) Prognosis depends greatly on stage, but overall is poor (5 yr survival: <5%) because many patients present with advanced disease. Patients with cancer restricted to the mucosa have about an 80% survival rate, which drops to <50% with submucosal involvement, 20% with extension to the muscularis propria, 7% with extension to adjacent structures, and <3% with distant metastases.

About 80 to 85% of all cervical cancers are squamous cell carcinoma. Diagnosis is by screening cervical Papanicolaou (Pap) test and biopsy. Staging is clinical. Treatment usually includes surgical resection, radiation therapy, and, unless cancer is localized, chemotherapy; if cancer is widely metastasized, treatment is primarily chemotherapy. Cervical cancer results from cervical intraepithelial neoplasia (CIN), which appears to be caused by infection with human papillomavirus (HPV) type 16, 18, 31, 33, 35, or 39.

CIN is graded as 1 (mild cervical dysplasia), 2 (moderate dysplasia), or 3 (severe dysplasia and carcinoma in situ). CIN 3 is unlikely to regress spontaneously; if untreated, it may, over months or years, penetrate the basement membrane, becoming invasive carcinoma. Invasive cervical cancer usually spreads by direct extension into surrounding tissues or via the lymphatics to the pelvic and para-aortic lymph nodes. Hematogenous spread is possible.

In squamous cell carcinoma, distant metastases usually occur only when the cancer is advanced or recurrent. The 5-yr survival rates are 80 to 90% with stage I, 50 to 65% with stage II, 25 to 35% with stage III, and 0 to 15% with stage IV. Nearly 80% of recurrences manifest within 2 yr. Adverse prognostic factors include lymph node involvement, large tumor size and volume, deep cervical stromal invasion, parametrial invasion, vascular space invasion, and nonsquamous histology.

Basal cell and squamous cell carcinomas may arise in the ear canal. Persistent inflammation from chronic otitis media may predispose to the development of squamous cell carcinoma. Extensive resection is indicated, followed by radiation therapy. En bloc resection of the ear canal with sparing of the facial nerve is performed when lesions are limited to the canal and have not invaded the middle ear.

Airway tumors can arise from primary tracheobronchial tumors, adjacent primary tumors with airway invasion, or metastatic disease to the airway. The most common malignant tracheal tumors include adenoid cystic carcinoma, squamous cell carcinoma, carcinoid, and mucoepidermoid carcinomas. The most common benign airway tumor is a squamous papilloma, although pleomorphic adenomas and granular cell and benign cartilaginous tumors also occur.

Prognosis depends on the histology. Squamous cell carcinomas tend to metastasize to regional lymph nodes and directly invade mediastinal structures, leading to high local and regional recurrence rates. Even with definitive surgical resection, the 5-yr survival is 20 to 40%.

Differential Cell Analysis

The presence of SCSC in a patient sample can be indicative of the stage of the carcinoma. In addition, detection of SCSC can be used to monitor response to therapy and to aid in prognosis. The presence of SCSC can be determined by quantitating the cells having the phenotype of the stem cell. In addition to cell surface phenotyping, it may be useful to quantitate the cells in a sample that have a "stem cell" character, which may be determined by the expression of Bmi1, or by functional criteria, such as the ability to self-renew, to give rise to tumors in vivo, e.g. in a xenograft model, and the like.

Clinical samples for use in the methods of the invention may be obtained from a variety of sources, particularly biopsy samples of squamous carincomas from patients, although in some instances samples such as bone marrow, lymph, cerebrospinal fluid, synovial fluid, and the like may be used. For analysis by histology methods, sections, which may be frozen, embedded, etc. are taken from a tumor sample. Once a sample is obtained, it can be used directly, frozen, or maintained in appropriate culture medium for short periods of time. The samples may be obtained by any convenient procedure. Typically the samples will be from human patients, although animal models may find use, e.g. equine, bovine, porcine, canine, feline, rodent, e.g. mice, rats, hamster, primate, etc. In some embodiments, where analysis by flow cytometry is desired, the tissue sample is dissociated, and the cell suspension may be separated by centrifugation, elutriation, density gradient separation, apheresis, affinity selection, panning, FACS, centrifugation with Hypaque, etc. prior to analysis.

The cell sample is contacted with reagents specific for markers that identify SCSC, as described above. The labeled cells are quantitated as to the expression of cell markers. A number of such methods are known in the art.

The comparison of a differential progenitor analysis obtained from a patient sample, and a reference differential progenitor analysis is accomplished by the use of suitable deduction protocols, AI systems, statistical comparisons, etc. A comparison with a reference tissue analysis from normal cells, cells from similarly diseased tissue, and the like, can provide an indication of the disease staging. A database of reference tissue analyses can be compiled. The methods of the invention provide detection of a predisposition to more aggressive tumor grow growth prior to onset of clinical symptoms, and therefore allow early therapeutic intervention, e.g. initiation of chemotherapy, increase of chemotherapy dose, changing selection of chemotherapeutic drug, and the like.

Cell Staining Methods

Analysis by cell staining may use conventional methods, as known in the art. Techniques providing accurate enumeration include confocal microscopy, fluorescence microscopy, fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, polynucleotide probes specific for an mRNA of interest, peptide-MHC antigen and T cell receptor pairs may be used; peptide ligands and receptor; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to cells, and incubated for a period of time sufficient to bind the available antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

Analysis may be performed based on in situ hybridization analysis, or antibody binding to tissue sections. Such analysis allows identification of histologically distinct cells within a tumor mass, and the identification of genes expressed in such cells. Sections for hybridization may comprise one or multiple solid tumor samples, e.g. using a tissue microarray (see, for example, West and van de Rijn (2006) Histopathology 48(1):22-31; and Montgomery et al. (2005) Appl Immunohistochem Mol Morphol. 13(1):80-4). Tissue microarrays (TMAs) comprise multiple sections. A selected probe, e.g. antibody specific for a marker of interest; or probe specific for Bmi1, is detectable labeled, and allowed to bind to the tissue section, using methods known in the art. The staining may be combined with other histochemical or immunohistochemical methods. The expression of selected genes in a stromal component of a tumor allows for characterization of the cells according to similarity to a stromal cell correlate of a soft tissue tumor.

The labeled cells are then analyzed as to the expression of cell surface markers as previously described.

SCSC Compositions

The cells of interest may be separated from a complex mixture of cells by techniques that enrich for cells having the above described characteristics. For isolation of cells from tissue, an appropriate solution may be used for dispersion or suspension. Such solution will generally, be a balanced salt solution, e.g. normal saline, PBS, Hank's balanced salt solution; etc., conveniently supplemented with fetal calf serum or other naturally occurring factors, in conjunction with an acceptable buffer at: low concentration, generally from 5-25 mM. Convenient buffers include HEPES, phosphate buffers, lactate buffers, etc.

The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscove's medium, etc., frequently supplemented with fetal calf serum.

Compositions highly enriched for SCSC are achieved in this manner. The subject population may be at or about 50% or more of the cell composition, and preferably be at or about 75% or more of the cell composition, and may be 90% or more. The desired cells are identified by their surface phenotype, by the ability to self-renew, ability to form tumors, etc. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. The population of cells enriched for SCSC may be used in a variety of screening assays and cultures, as described below.

The enriched SCSC population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI-1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. A wide variety of growth factors may be used in culturing the cells, e.g. LIF, steel factor (c-kit ligand), EGF, insulin, IGF, Flk-2 ligand, IL-11, IL-3, GM-CSF, erythropoietin, thrombopoietin, etc In addition to, or instead of growth factors, the subject cells may be grown in a co-culture with fibroblasts, stromal or other feeder layer cells. Stromal cells suitable for use in the growth of hematopoietic cells are known in the art. These include bone marrow stroma as used in "Whitlock-Witte" (Whitlock et al. [1985] *Annu Rev Immunol* 3:213-235) or "Dexter" culture conditions (Dexter et al. [1977]. *J Ex Med* 145:1612-1616); and heterogeneous thymic stromal Screening Assays SCSC are also useful for in vitro assays and screening to detect factors and chemotherapeutic agents that are active on cancer stem cells. Of particular interest are screening assays for agents that are active on human cells. A wide variety of assays may be used for this purpose, including immunoassays for protein binding; determination of cell growth, differentiation and functional activity; production of factors; and the like.

In screening assays for biologically active agents, anti-proliferative drugs, etc. the SCSC composition, usually a culture comprising SCSC, is contacted with the agent of interest, and the effect of the agent assessed by monitoring output parameters, such as expression of markers, cell viability, and the like. The cells may be freshly isolated, cultured, genetically altered, and the like. The cells may be environmentally induced variants of clonal cultures: e.g. split into independent cultures and grown under distinct conditions, for example with or without drugs; in the presence or absence of cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical: carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniues* 26(1):112-225; Kawamoto et al. (1999) *Genome Res* 9(12):1305-12; and Chen et al. (1998) *Genomics* 51(3):313-24, for examples.

Kits may be provided, where the kit will comprise a staining reagents that are sufficient to differentially identify the SCSC described herein. A marker combination of interest may include CD44 and a lineage panel as described herein. In other embodiments, a probe or antibody specific for Bmi1 may be included. The staining reagents are preferably antibodies, and may be detectably labeled. Kits may also include tubes, buffers, etc., and instructions for use.

Each publication cited in this specification is hereby incorporated by reference in its entirety for all purposes.

It: is to be understood that this invention is not limited to the particular methodology, protocols, cell lines, animal species or genera, and reagents described, as such may vary. It: is also to be understood that the terminology used herein is for the purpose of describing particular embodiments only, and is not intended to limit the scope of the present invention, which will be limited only by the appended claims.

As used herein the singular forms “a”, “and”, and “the” include plural referents unless the context clearly dictates otherwise. Thus, for example, reference to “a cell” includes a plurality of such cells and reference to “the culture” includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Experimental

Like many epithelial tumors, head and neck squamous cell carcinoma (HNSCC) contains a heterogeneous population of cancer cells. We developed an immunodeficient mouse model to test the tumorigenic potential of different populations of cancer cells derived from primary, unmanipulated human HNSCC samples. We show that a minority population of CD44+Lineage− cancer cells, which typically comprise less than 10% of the cells in a HNSCC tumor, but not the CD44−Lineage− cancer cells gave rise to new tumors in vivo. Immunohistochemistry revealed that the CD44+ cancer cells have a primitive cellular morphology, and costain with the basal cell marker Cytokeratin 5/14, while the CD44− cancer cells resemble differentiated squamous epithelium, and express the differentiation marker Involucrin.

The tumors that arose from purified CD44+Lineage− cells reproduced the original tumor heterogeneity, and they could be serially passaged, thus demonstrating the 2 defining properties of stem cells: the ability to self renew and to differentiate. Furthermore, the tumorigenic CD44+Lineage− cells differentially express the Bmi1 gene, both at the RNA and protein levels. By immunohistochemical analysis the CD44+ cells in the tumor express high levels of nuclear Bmi1, and are arrayed in characteristic tumor microdomains. This data demonstrates that cells within the CD44+Lineage− population of human HNSCC possess the unique properties of cancer stem cells in functional assays for cancer stem cell self-renewal and differentiation, and form unique histological microdomains that can aid in cancer diagnosis.

In this study we show that HNSCC contains a distinct population of cancer cells, with the exclusive ability to produce tumors in mice and recreate the original tumor heterogeneity. We have identified a cell surface marker that can enrich for this cell population and have provided evidence that this population possesses properties classically attributed to stem cells. We have also identified a gene previously implicated in self-renewal and tumorigenesis, Bmi1, that is differentially expressed at both the RNA and protein levels in the tumorigenic cell population, and in tissue sections defines microdomains of cancer stem cells that are membrane CD44+ and nuclear Bmi1+. This both provides insight into the possible molecular mechanisms mediating the self-renewal of these cells, as well as demonstrating the value of identifying the CSC population in primary tumors in order to further characterize these cells at the molecular level and thus develop new treatment strategies targeted against this critical population of cancer cells.

Results

A mouse xenograft model of HNSCC was developed in which primary specimens obtained from patients undergoing surgical resection were implanted under the skin of immunocompromised mice, either NOD/SCID or Rag2/common cytokine receptor common gamma chain double knockout (Rag2γDKO), either as small (<2 mm) pieces of tumor, or as cell suspensions in matrigel, ranging from 1 to 5 million total cells per injection. Of 25 samples of HNSCC tumors implanted in this way, 13 have given rise to tumors in the mice. Both the NOD/SCID (UM) and Rag2γDKO (SU) mouse model gave similar rates of tumor engraftment. These results indicate that either animal model is reliable.

When solid tumor pieces were implanted into the mice, a small tumor nodule was evident in 6-10 weeks on average and reached a size of 1-1.4 cm in 4-6 months on average. Single cell suspensions produced small tumor nodules in 8-12 weeks depending on the number of cells injected. Of the tumor specimens that grew in mice, 9 were subjected to flow cytometry on cells obtained either immediately after removal from the patient (UMHN3,5,6,7), or from tumors arising in the immunodeficient mice (UMHN1, UMHN2, UMHN4, SUHN1 and SUHN2) to obtain purified populations of tumor cells for further transplants.

It was not possible to use cells obtained directly from patient samples in all cases, as the specimens obtained from the clinic were frequently too small to obtain sufficient numbers of cells for these experiments. These nine subjects ranged in age from 22 to 72 years old. Three tumor specimens were harvested from the tongue, two each from the larynx and floor of mouth, and one each from the oropharynx and maxillary sinus. Three subjects had undergone previous treatment for their cancer greater than one year prior to this study. The degree of differentiation, evaluated by histologic architecture, varied from poor- to well-differentiated (Table 1).

TABLE 1

Patient demographics

| Sample | Age | Sex | Tumor site | Stage | Differentiation | Previous Treatment |
|---|---|---|---|---|---|---|
| UMHN1 | 72 | M | Oropharynx | T4aN2a | Well | None |
| UMHN2 | 69 | M | Tongue | T3N3 | N/A | None |
| UMHN3 | 52 | F | Tongue | T2N0 | Poor | s, c, r |
| UMHN4 | 54 | M | Larynx | T4N2c | Poor | c, r |
| UMHN5 | 88 | M | Floor of Mouth | T2N2b | Moderate | None |
| UMHN6 | 78 | M | Larynx | T4N0 | N/A | c, r |
| UMHN7 | 53 | F | Floor of Mouth | T2N2c | Moderate | None |
| SUHN1 | 71 | M | Maxillary Sinus | T4aN0 | Moderate-to-poor | None |
| SUHN2 | 22 | M | Tongue | T3N0 | Moderate | None |

s—surgical resection c, r—combined chemotherapy and radiation therapy

Flow cytometry analysis revealed that the HNSCC specimens were heterogeneous with respect to the cell surface marker CD44 (FIG. 1). Antigens associated with normal cell types (lineage markers CD2, CD3, CD10, CD18, CD31, CD64 and Q140b) were not expressed on the cancer cells. These lineage markers were used to eliminate normal leukocytes, fibroblasts endothelial, and mesothelial cells (Lineage+) from the tumor specimens during the cell sorting experiments. In passaged tumors mouse anti-H2K antibodies were used to eliminate contaminating mouse cells.

In each tumor a distinct population of CD44 positive (CD44+) and CD44 negative CD44− cancer cells was identifiable. Importantly, similar results were obtained from tumors that had been passaged once through mice before sorting as from tumors analyzed directly from patients, indicating that a single passage did not significantly effect the expression of this marker. Single cell suspensions of purified CD44+Lineage− and CD44−Lineage− cells at different doses were implanted into the mouse model to determine whether CD44 status could distinguish between tumorigenic and non-tumorigenic cells (Table 2).

TABLE 2

Growth of HNSCC tumors in mice injected with single cell suspensions of CD44+Lineage- or CD44−Lineage- cells

| Sample | | Cell Count | | | | | | | |
|---|---|---|---|---|---|---|---|---|---|
| (% CD44+) | Population | 500-650K | 200-300K | 100-150K | 40-50K | 20-25K | 10K | 5K | 2K |
| UMHN1* | CD44+ | | 1/1 | | | | | | |
| (13.4) | CD44− | 0/1 | | | | | | | |
| UMHN2* | CD44+ | | | | 2/2 | | 1/2 | 1/1 | |
| (16.4) | CD44− | | 0/2 | | 0/1 | | | | |
| UMHN3** | CD44+ | | | | 1/1 | | | 3/3 | |
| (12.0) | CD44− | | 0/3 | 0/3 | 0/3 | | | | |
| UMHN4* | CD44+ | | | 1/1 | | | | | |
| (10.4) | CD44− | | 0/1 | | | 0/1 | 0/1 | 0/1 | |
| UMHN5** | CD44+ | | | | 1/1 | | 1/1 | 1/2 | |
| (0.43) | CD44− | 0/1 | | | | | | 0/2 | |
| UMHN6** | CD44+ | | | | | | 1/1 | 0/1 | |
| (1.7) | CD44− | | | 0/2 | | | | | |
| UMHN7** | CD44+ | | | 1/1 | | | | | 0/1 |
| (5.2) | CD44− | 0/1 | | | | | | | |
| SUHN1* | CD44+ | | | | 3/3 | 1/2 | 0/1 | 0/4 | 0/1 |
| (35.1) | CD44− | | | | 1/6 | 0/2 | 0/2 | 0/2 | 0/1 |
| SUHN2* | CD44+ | | | | | | | 1/1 | |
| (1.3) | CD44− | | | | 0/1 | 0/2 | 0/1 | | |

*Samples that were passaged once through mice prior to sorting for CD44+ and CD44− populations

**Samples that were directly sorted from patient samples for CD44+ and CD44− populations.

UMHN samples were all grown in NOD/SCID mice

SUHN samples were all grown in Rag?DKO mice

Initial data from UM (UMHN1) using large numbers of implanted cells indicated that CD44+ cells could form tumors while CD44− cells could not. Similarly, initial data from SU (SUHN1) indicated that, at equivalent doses of cells, CD44+ cells initiated tumor growth much more efficiently than CD44− cells. In subsequent experiments larger numbers of CD44− cells were injected than CD44+ cells, on the assumption that this would increase the likelihood of detecting any tumor-initiating cells that may be present, but rare, within the CD44− population. In all cases, the number of cells injected, the range of cell doses, and the number of mice injected with each dose was severely limited by the number of cells that could be sorted from primary and first passage tumors.

In the tumors analyzed in this study, a total of 20/31 injections of CD44+ cells formed tumors, while only 1/40 injections of CD44− cells did so ($p<6\times10^{-9}$, Fisher's Exact Test). In both the NOD/SCID mice and the Rag2γDKO mice the CD44+ cells had a significantly greater tumorigenic capacity than the CD44− cells. This indicates that the CD44 status of the cells was the determining factor for tumor growth, not the animal model used. As few as $5\times10^3$ CD44+Lineage− cells obtained directly from a patient's tumor or from early passage xenograft tumors gave rise to new tumors (Table 2). In contrast up to $5\times10^5$ CD44− cells failed to form tumors. When greater than $4\times10^4$ CD44+ Lineage− HNSCC cells were injected, tumors formed within 10-16 weeks (7/7). In experiments where $5\text{-}25\times10^3$ CD44+Lineage− HNSCC cells were injected, tumors formed in ten out of 17 injections.

No detectable tumors developed at any dose of CD44−Lineage− cells, with one exception (1/40 ). The latter case occurred early in the study, in an experiment where cells were sorted only once, and the tumor could have arisen as a result of contamination of the CD44− population with a small number of CD44+ cells. This is further indicated by the fact that the tumor in question was approximately 3-fold smaller than the tumor initiated by an equivalent dose of CD44+ cells. In all other experiments, cells were double-sorted, yielding a population purity of >95%. Even after greater than 24-48 weeks CD44−Lineage− injection sites revealed no detectable tumor growth, even though this class of cells can be derived from the tumorigenic CD44+Lin− cells (see below). Implanted Lineage+ cells did not grow any tumors in the mouse model. Again, the similarity in results obtained with primary patient cells versus cells from passaged tumors indicated that passaging did not change the expression pattern of CD44 in HNSCC tumors, nor the differential tumorigenicity of this population of cells.

Figure 2:
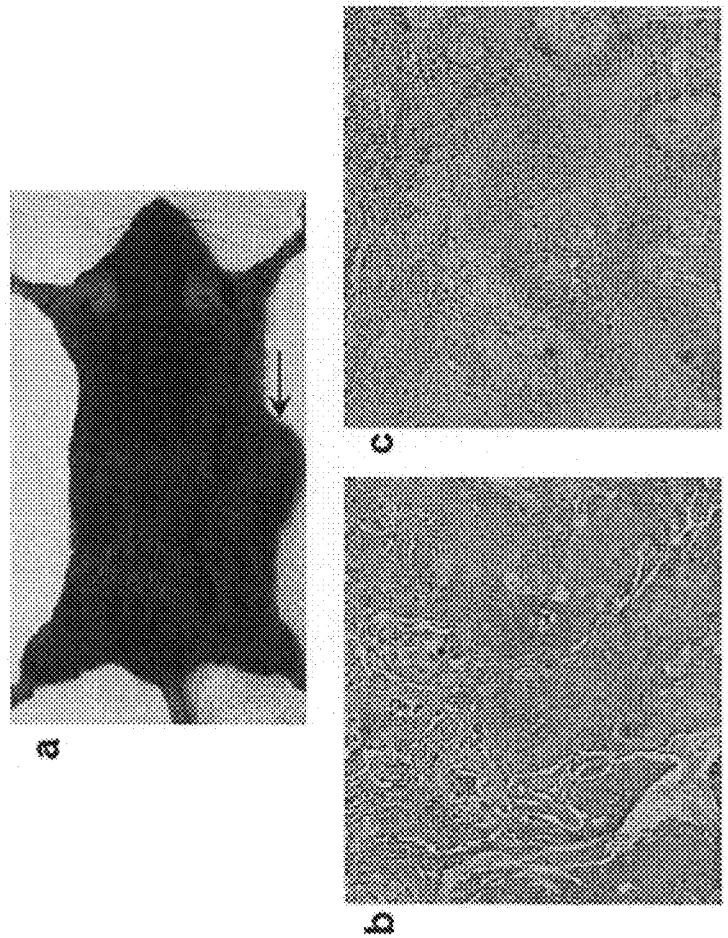
FIG. 2: Tumor Morphology. (a) Representative tumor in a mouse at the CD44+ injection site. (b) Histology of the tumor resulting from a CD44+ injection site (×20 objective magnification) and for comparison (c) histology from the corresponding primary tumor (×10 objective magnification).
Figure 3:
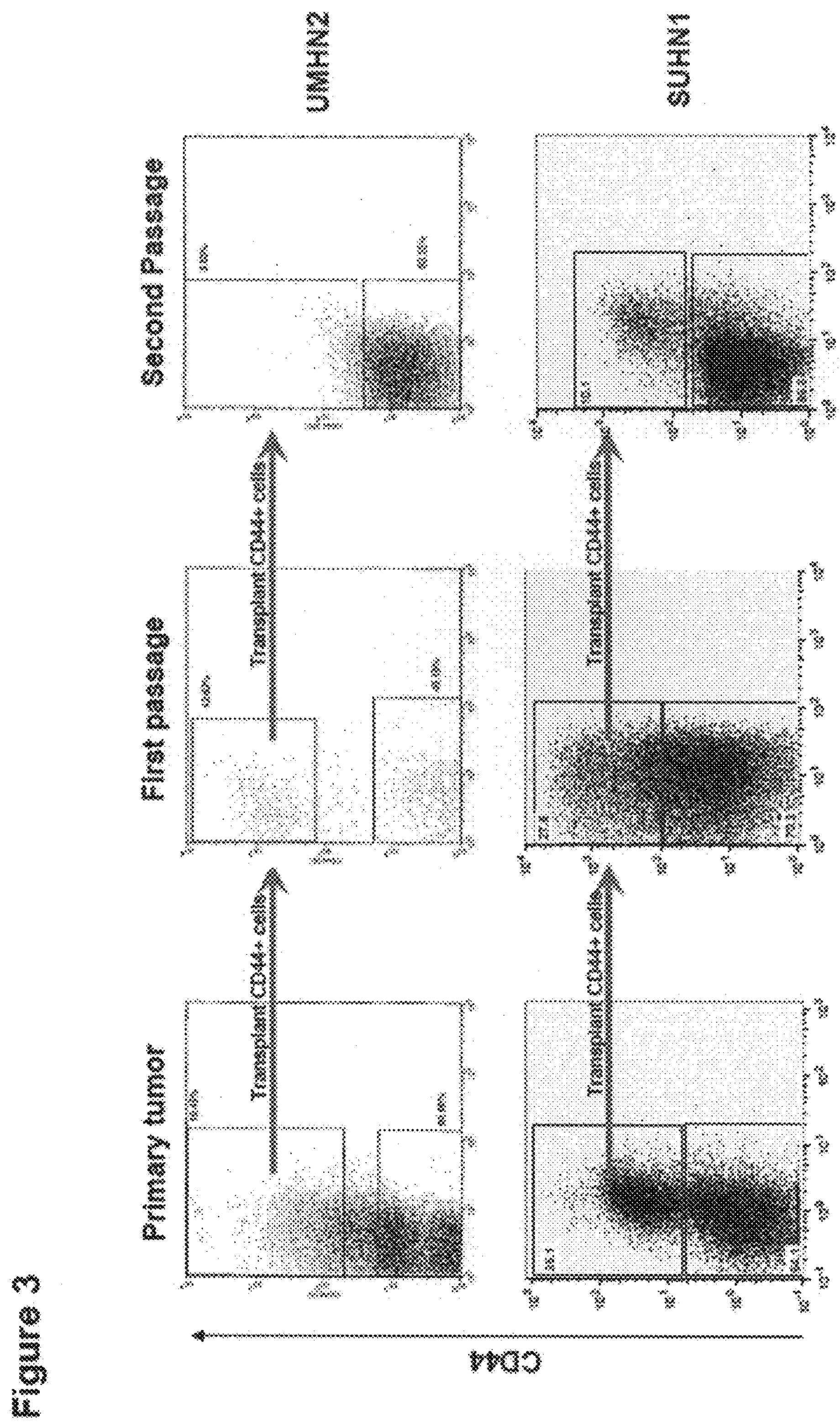
FIG. 3: Representative plots revealing the phenotypic diversity in tumors arising from CD44+ Lineage− cells in UMHN2 and SUHN1. The plots depict the CD44 staining pattern of live cancer cells from primary unpassaged tumor, tumor resulting from the implantation of CD44+ Lineage− cells from the primary tumour (first passaged tumor) and tumor resulting from the implantation of CD44+ Lineage− cells from the once passaged tumor (second passage tumor).

Tumors resulting from implanted CD44+ cells reproduced the original tumor morphology upon histologic examination (FIG. 2). Furthermore, analysis of tumors arising from implantation of CD44+Lineage− cells revealed that these cells gave rise to new tumors that contained cells that were again phenotypically diverse for CD44 expression. This indicates that the CD44+ cells within the tumor can give rise to more CD44+ cells, as well as CD44− cells. Upon resorting and passaging of the CD44+Lineage− and CD44−Lineage− populations, again only CD44+Lineage− cells initiated new tumors. CD44+Lineage− cells from UMHN4 and SUHN1 have been successfully serially passaged through two rounds of tumor formation. CD44+Lineage− cells from UMHN2 and SUHN1 (FIG. 3) have been passaged through three rounds of tumor formation in mice. CD44−Lineage− cells selected from passaged tumors never resulted in new tumor formation. Analysis of the passaged tumors by flow cytometry, after each successive sort and implantation, confirmed that the resulting tumors again contained both CD44+ and CD44− cells. The difference in the time after transplantations at which the tumors were harvested may account for the difference in the percent of CD44+ cells seen in the first and second passage tumors (9-10 weeks and 16 weeks, respectively).

Figure 4:
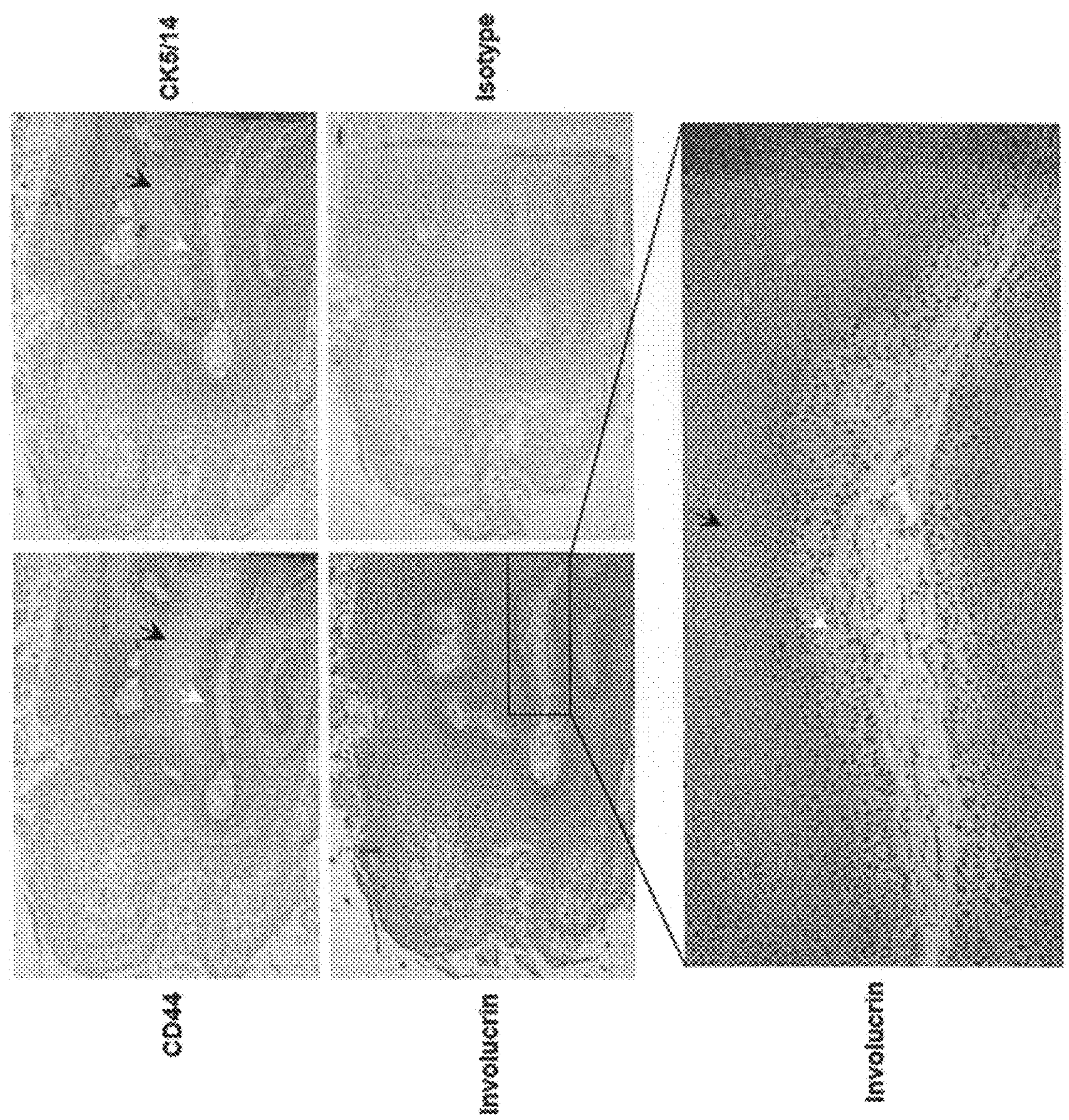
FIG. 4: Immunohistochemical Analysis of Well-Differentiated HNSCC. Serial sections were stained with antibodies to CD44, cytokeratin 5/14, Involucrin, or an isotype control. A horseradish peroxidase conjugated secondary antibody was used for detection. CD44+ regions were CK5/14+ and Involucrin− (white arrows), while CD44− regions were CK5/14− and Involucrin+ (black arrows).

In addition to the 9 tumor samples described above, additional tumors (those that did not take in the mouse model, and those that were too small to provide sufficient cell numbers for the xenograft experiments) were analyzed by flow cytometry and immunohistochemistry (IHC) for CD44 expression (Table 3, FIG. 4).

The majority of HNSCC contain a subpopulation of CD44+ cells, with the percentage of CD44+Lineage− cells in the tumors varying from 0.1% to 41.72%, n=33 (Table 3). 9 out of 33 samples analyzed had less than 1% of the cells expressing CD44. Immunohistochemistry for CD44 was performed to determine the physical location of the tumorigenic population of cells within the tumor. In the case of moderate-to-well-differentiated HNSCC samples, where a clear hierarchy of cell differentiation is present within the tumor (i.e. primitive basal layer cells and cells with the phenotype of differentiated keratinocytes), CD44 expression was detected in the basal layer, but not in the differentiated cells (FIG. 4).

TABLE 3

CD44 expression of all HNSCC samples analyzed to date

| Stanford University | | University of Michigan | |
|---|---|---|---|
| Sample | % CD44+ | Sample | % CD44+ |
| 1(SUHN1) | 35.1 | 1(UMHN1) | 13.4 |
| 2 | 0.2 | 2 | 0.1 |
| 3 | 1.2 | 3(UMHN2) | 16.4 |
| 4 | 15.2 | 4 | 5.2 |
| 5 | 1.8 | 5(UMHN3) | 12.0 |
| 6 | 11.8 | 6 | 0.2 |
| 7(SUHN2) | 1.3 | 7(UMHN4) | 10.4 |
| 8 | 5.2 | 8(UMHN5) | 0.43 |
| 9 | 9.0 | 9 | 0.2 |
| 10 | 1.0 | 10 | 14.0 |
| 11 | 11.2 | 11 | 41.7 |
| 12 | 0.6 | 12 | 0.8 |
| 13 | 7.5 | 13 | 1.2 |
| 14 | 23.7 | 14 | 2.0 |
| 15 | 0.4 | 15 | 1.2 |
| 16 | 17.1 | 16(UMHN6) | 1.7 |
| | | 17(UMHN7) | 5.2 |

Corresponding samples from Table 2 are indicated

To confirm that the basal cell layer represented undifferentiated cells, serial sections stained with an antibody to Cytokeratin 5/14 (CK5/14), a basal layer marker; or with and antibody to Involucrin, a differentiated keratinocyte marker. It was found that CD44 costained with CK5/14, whereas CD44 and Involucrin staining were mutually exclusive. It was also clear on these sections that the Involucrin+CD44− cells in these tumors retained the differentiated phenotype of mature or maturing squamous epithelium, whereas the Involucrin-CD44+ cells have a basaloid phenotype. The latter data was confirmed on 4 moderate-to-well-differentiated primary patient tumors.

At this point it appeared that the CD44+Lineage− population of tumor cells is enriched for a population of cells that functionally have properties of cancer stem cells: they are highly tumorigenic, they self-renew as demonstrated by serial transplantation, their physical location and morphology in tissue sections is analagous to the stem/progenitor cell population of the corresponding normal tissue, and they give rise to large numbers of progeny that have limited to no proliferative potential (the CD44− Lineage− cells) and that express differentiation markers (Involucrin).

Figure 5:
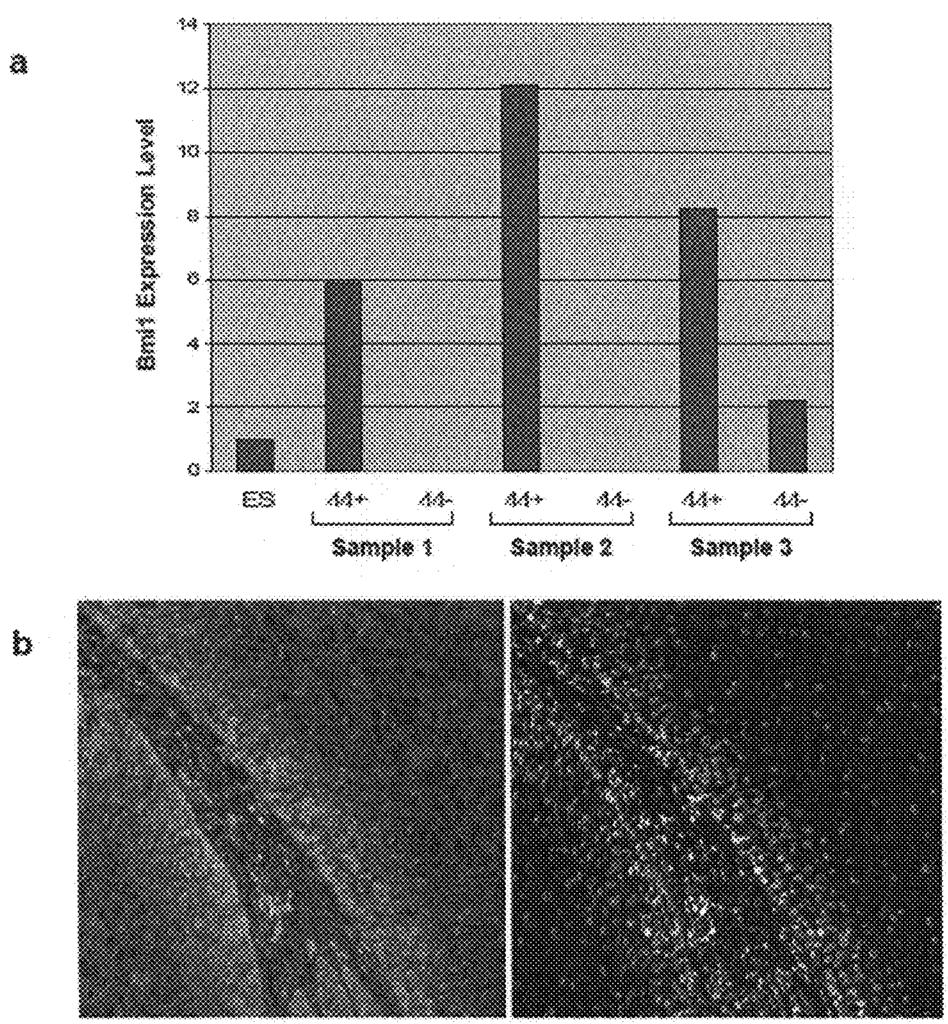
FIG. 5: Quantitative RT-PCR and Immunofluorescence for Bmi1. (a) CD44+Lineage and CD44−Lineage− cells from 3 HNSCC samples were double-sorted and purified RNA was assayed for the presence of Bmi1 transcripts by quantitative RT-PCR. Human embryonic stem cells (ES) were used as a positive control for PCR, and transcript levels were normalized to expression of β-actin. All 3 samples were primary patient samples. Bmi1 was expressed in the CD44+Lineage− population but was undetectable in the CD44−Lineage− population in samples 1 and 2, and 4-fold lower in the CD44− Lineage population in sample 3. (b) A well-differentiated HNSCC, was costained for CD44 (green) and Bmi1 (red). On the left, the CD44/Bmi1 overlay is shown, and on the right the Bmi1/Hoechst 33342 overlay, to highlight nuclei in blue, is shown. Bmi1 protein was seen in the nuclei of the majority of CD44+ cells, and was rare in the CD44− region of the tumor.

We then decided to investigate the properties of these cells at the level of gene expression. CD44+Lineage− and CD44− Lineage− cells were sorted for RNA purification, and quantitative RT-PCR was performed for a variety of stem cell-related genes. In 3 primary patient samples, it was found that Bmi1 was expressed at high levels compared to human ES cells in the CD44+ population, but was undetectable in the CD44− population in 2 of the 3 samples, and 4-fold lower in the third sample (FIG. 5). Expression of β-actin was used as a control for RNA quality, and the data is shown relative to β-actin expression. We then performed immunofluorescent costaining for CD44 and Bmi1 on tissue sections and found that the Bmi1 protein was present in the nuclei of the CD44+ cells of the tumors, particularly in the most basal regions, and rarely seen in the CD44− regions of the tumors. This result was obtained for 4 different primary patient samples that were analyzed in this way (FIG. 5).

Discussion

The CSC hypothesis suggests that only the CSC and not the heterogeneous mix of cells within the tumor can self-renew and proliferate extensively to form new tumors. It has been demonstrated for several different types of cancer that a distinct subset of cells initiates tumors in vivo, while the remaining cells do not. Further evidence for the CSC hypothesis comes from clinical observations, where tumors often respond to chemotherapy initially, but frequently recur, suggesting that residual stem cells remaining after therapy are responsible for tumor regeneration. In HNSCC, as in other cancers, characterization of cancer stem cells allows for the development of new treatments that are specifically targeted against this critical population of cells, particularly their ability to self-renew, resulting in more effective therapies.

In this study we have provided evidence for the existence of a developmental hierarchy within human HNSCC; that is, HNSCC contain a subpopulation of tumorigenic cancer cells with both self-renewal and differentiation capacity. These tumorigenic cells are responsible for tumor maintenance, and also give rise to large numbers of abnormally differentiating progeny that are not tumorigenic, thus meeting the criteria of cancer stem cells.

Our initial finding was that all tumorigenic potential was contained within the CD44+ Lineage− population of HNSCC. The ability to initiate tumor growth with cell doses ranging from 5000 to 20000 of these cells, combined with the need to inject at least $1\times10^6$ cells to obtain tumors from whole tumor cell suspensions, and the lack of tumor formation by CD44− Lineage− cells at much higher cell doses, provided the strongest evidence that the CD44+ Lineage− population contains the HNSCC stem cell population within it.

Upon reanalysis of tumors arising from the transplantation of purified CD44+ cells, both CD44+ and CD44− cells were again present, indicating that tumorigenic CD44+ cells give rise to nontumorigenic CD44− cells. Furthermore, serial transplants demonstrate that with each tumor passage, only CD44+Lineage− and not the CD44− Lineage− cells can initiate a new tumor. Each time, the tumor again contains a mixture of CD44+ and CD44− cells. Over multiple transplants, a large expansion of the CD44+ population occurs that can only be accounted for by self-renewal of the tumorigenic population. Self-renewal is a hallmark property of stem cells.

Further evidence for a developmental hierarchy in HNSCC comes from the histology and immunohistochemistry studies done on moderate-to-well differentiated tumors. First, the tumors demonstrate cytologic and archictectural features similar to normal squamous epithelium, including differentiation from a basal layer towards an apical layer containing cells with mature squamous morphology, and the formation of keratin (keratin pearls were present). Second, CD44 clearly stains regions of the tumors that have basal cell morphology and that costain with the basal layer marker CK5/14. Finally, the differentiation marker Involucrin stains the regions of the tumor that are negative for CD44, and vice versa.

Quantitative RT-PCR combined with immunofluorescent staining of tumor sections indicates that the tumorigenic population of cells differentially expresses the gene Bmi1. Bmi1 has been shown to play a role in the self-renewal of hematopoietic and, neuronal stem cells, and is considered to be a stem cell-related gene. Bmi1 has also been implicated in tumorigenesis, primarily in leukemias, but also in several human cancers, including colorectal carcinoma, liver carcinomas, and nonsmall cell lung cancer. The combination of CD44 positive staining at the cell membrane and Bmi1 staining in the nucleus allows the definition of HNSCC cancer stem cell microdomains in the primary tumor, and may be useful in diagnosis of HNSCC in primary sites, as well as cells in lymph node or distant metastases.

In summary, we have demonstrated that, in HNSCC, there exists a developmental hierarchy, including a population of cells that possess the properties of cancer stem cells (they form tumors in vivo, they self-renew, they give rise to abnormally differentiated, nontumorigenic progeny, and they differentially express at least one stem cell-associated gene). This population can be enriched by selecting for cells that express the cell surface marker CD44. The remaining CD44− tumor cells, that make up the majority of cells in the tumor, have properties of more mature cells with limited proliferative capacity (they don't form tumors in vivo, they are morphologically partially-to-well-differentiated, they express differentiation markers, and they don't express Bmi1).

In addition to the significance of this work to the study of HNSCC, our findings have two major implications to the field of cancer biology in general. First, this is the second epithelial tumor in which CD44 has been identified as a key cell surface marker of CSC (breast cancer being the first), suggesting that CD44 is likely to be an important marker for the identification of cancer stem cells in other tumors of epithelial origin. Second, we demonstrate that genes with potentially important biological activities can be identified that are differentially expressed between subpopulations of tumor cells, thus emphasizing the importance of identifying and isolating the appropriate subpopulations of tumor cells prior to performing large-scale gene expression and proteomic analyses. In the case of samples where the CSC make up a small fraction (10% or less) of the tumor cells, in combination with the fact that the genes of interest may be typically expressed at low levels (e.g. transcription factors), analyses of whole tumors may not detect the most important molecular players in the etiology and pathology of cancer.

Materials and Methods

After obtaining informed consent, as approved by the respective institutional Internal Review Boards, primary tumors were obtained from subjects at either the University of Michigan (UM) or Stanford University (SU) hospitals. Animal care and experimental protocols were performed in accordance with procedures and guidelines established by the Stanford University and University of Michigan Administrative Panels for Lab Animal Care for the humane care and use of animals. Experiments conducted at the University of Michigan utilized a NOD/SCID mouse model, and experiments at Stanford University used a Rag2/common cytokine receptor common gamma chain double knockout (Rag2γDKO) mouse model.

Primary tumor implantation. The fresh tumor specimens on ice were received within an hour of extraction from the operating room in Media 199. Small pieces of tumor were chopped into 2-mm pieces with scissors. Female NOD/SCID (UM) or Rag2γDKO (SU) mice were injected intraperitoneally with ketamine/xylazine anesthetic at 0.02 mL/20 g (300 mg ketamine combined with 20 mg xylazine in 4 mL of PBS). An approximately 3-mm incision was made and small pieces of solid tumor were implanted in both sides of the base of the neck or the flank with a trocar. Tumors were pinched into their final position in the mouse and the incision was sealed with a liquid adhesive suture or a surgical staple. Alternatively, single cell suspensions were generated and injected subcutaneously, as described below.

Tumor Digestion. Primary tumors were cut into small fragments with sterile scissors and then further minced with a sterile scalpel. The tumor pieces were rinsed with Hanks balanced salt solution (HBSS) and centrifuged for 5 min at 1000 rpm and placed in a solution of Media 199 and 200 U/mL Collagenase III. The mixture was incubated at 37° C. for up to 3 hours to allow complete digestion. Every 15 minutes, the solution was mixed through a 10-mL pipette to dissociate cells in the tumor pieces. The digestion was arrested with the addition of Fetal Bovine Serum and then cells were filtered through 40-μm-nylon mesh. The suspended cells were washed twice with HBSS/2% Heat Inactivated Calf Serum (HICS) and stained for flow cytometry or injected into mice as whole tumor single cell suspensions, as described below.

Single cell suspension injections. Mice were anesthetized in the same manner as the tumor implantation procedure (UM) or by inhalation of isoflurane (SU). Up to 2 million cells were washed in HBSS/2% HICS and then suspended in 100-μL of RPMI 1640. The cells were then mixed in a 1:1 ratio with Matrigel (BD Pharmingen) solution to form a final volume of 200-μL. The mice were then injected subcutaneously at the base of the neck (UM) or the flank (SU) with the suspension.

Flow Cytometry. The single cell suspensions were washed in HBSS/2% HICS and the cells were counted. The cells were resuspended in 100 μL/$10_6$ cells of HBSS and incubated with 1 mg/mL of Sandoglobin for 10 minutes. The single cell suspension was then washed twice with HBSS/2% HICS, resuspended in 100 μL/$10_6$ cells of HBSS and stained with antibodies. Anti-CD44 (Pharred, phycoerythrin (PE) or allophycocyanin (APC) conjugated, clone G44-26; BD Pharmingen) was added at the appropriate dilution per antibody and incubated for 20 minutes on ice. The cells were also stained with lineage markers anti-CD2, CD3, CD10, CD16, CD18, CD31, CD64, and CD140b (all from BD Pharmingen) to allow identification of contaminating non-tumor cells. Tumor cells that had been passaged in the mouse were incubated with anti-H2 $k_d$ or H2 $k_b$ (BD Pharmingen). Antibodies were directly conjugated to various fluorochromes, depending upon the experiment. Stained cells were then washed 2 times with HBSS/HICS and resuspended at 0.5 mL/$10_6$ cells. 7-aminoactinomycin (7-AAD, BD Pharmingen) or propidium iodide was added at the appropriate dilution to allow for the removal of nonviable cells. The single cell suspension was sorted with a BD FACSVantage flow cytometer. In all experiments dead cells and nontumor (Lineage+) or mouse cells were eliminated by flow cytometry. Forward and side scatter profiles were utilized to remove cell doublets. All cells were reanalyzed and sorted twice to ensure purity of >95%.

Immunohistochemistry (IHC) and Immunofluorescence (IF) Upon receipt of a tumor specimen, a small piece was kept aside and frozen in O.C.T embedding media. 7 ſ m sections were cut, fixed in ice cold acetone for 5 minutes and air-dried. Slides were then rinsed in PBS/0.1% Tween, and blocked in PBS with 0.5% bovine serum albumin (BSA), and in the case of IHC, 0.3% hydrogen peroxide, and 0.1% sodium azide. For CD44 staining, 20 ſ g/ml of mouse IgG was added to the blocking solution. For Cytokeratin 5/14 (CK5/14), Involucrin, and Bmi1, 5% goat serum was added to the blocking solution. Sections were incubated in blocking solution at room temperature (RT) for 30 minutes. Sections were then incubated with the primary antibody diluted in PBS with 0.5% BSA for 30 minutes at room temperature. For Bmi1, sections were incubated overnight at 4° C. For CD44 staining, biotinylated clone G44-26 (Pharmingen) was used at a dilution of 1:50. For CK5/14, unconjugated clone LH8 (Abcam) was used at a dilution of 1:100. For Involucrin, unconjugate clone SY5 (Abcam) was used at a dilution of 1:200. For Bmi1, unconjugated clone 1.T.21 (Abcam) was used at a dilution of 1:100. The slides were then washed twice in PBS with 0.1% Tween, 5 minutes each. A secondary incubation of 30 minutes at RT was then performed with 1:1000 Avidin-HRP (Pharmingen) or 1:400 Avidin-Alexa488 (Molecular Probes), 1:200 biotinylated goat-anti-mouse IgM (Jackson Immunoresearch), or biotinylated 1:1000 goat-anti-mouse IgG (Jackson Immunoresearch), or 1:200 goat-anti-mouse IgGAlexa594, for CD44, CK5/14 Involucrin, and Bmi1, respectively. Slides were again washed, and for CK5/14 and Involucrin, a tertiary incubation with Avidin-HRP was performed. The sections were then incubated with 3,3.-diaminobenzidine (DAB), as directed by the manufacturer (Vector Laboratories peroxidase substrate kit), counterstained with hematoxylin, dehydrated and coverslipped with histomount for IHC. For IF, double staining was done sequentially as follows: Blocking, unconjugated Bmi1, goat-anti-mouse-Alexa594, CD44- biotin, Avidin-Alexa488. Slides were then immersed in 1:1000 Hoechst 33342 (Invitrogen) for 1 minute, rinsed in PBS/0.1% Tween, and coverslipped with Fluoromount G (Southern Biotech).

Quantitative RT-PCR Sorted cells were pelleted, resuspended in 1 ml of Trizol (Invitrogen) and incubated on ice for 10 mins. 2ſ 1 of linear acrylamide (Ambion) were added and mixed, and RNA was purified by standard techniques. cDNA was then synthesized using the Superscript Double-Stranded cDNA Synthesis Kit (Invitrogen), as directed by the manufacturer. cDNA was diluted to give 200 cell-equivalents per microliter. For quantitative PCR, Applied Biosystems gene expression assays were used, which contain prevalidated primers and TaqMan probes for the individual genes in question. PCR was performed as instructed by the manufacturer on an ABI 7500 real-time PCR system (Applied Biosystems). cDNA isolated from undifferentiated human embryonic stem cells was used as a positive control, and gene expression was normalized to β-Actin expression.

What is claimed is:

1. A method for characterizing a head and throat squamous carcinoma from a patient, the method comprising:

(a) contacting a sample of said head and throat squamous carcinoma with reagents that bind CD44, reagents that bind lineage markers CD2, CD3, CD10, CD16, CD18, CD31, CD64, and CD140b, and reagents that bind involucrin, and one or both of CK5 and/or CK14, wherein said head and throat squamous carcinoma sample is CK5/14 positive and involucrin negative;

(b) quantitating the number of CD44 positive, lineage marker negative cancer cells; and (c) identifying cancer stem cells as CD44 positive, lineage marker negative cancer cells of head and throat squamous carcinoma.

2. The method according to claim 1, further comprising contacting said sample with a reagent that binds Bmi1, and wherein squamous carcinoma stem cells express Bmi1.

3. The method of claim 2, wherein the nuclear localization of Bmi1 is determined.

4. The method according to claim 3, wherein said sample is a section from a tumor biopsy.

5. The method according to claim 1, wherein said patient is a human.

6. The method of claim 1, wherein the quantitating is performed by flow cytometry.

7. The method of claim 1, wherein the quantitating is performed by immunohistochemistry.

8. A method for characterizing a head and throat squamous carcinoma from a patient, the method comprising:

(a) performing immunohistochemistry on a section from a tumor biopsy of head and throat squamous carcinoma with reagents that bind CD44, reagents that bind lineage markers CD2, CD3, CD10, CD16, CD18, CD31, CD64, and CD140b, and reagents that bind involucrin, and one or both of CK5 and/or CK14, wherein said head and throat squamous carcinoma tumor biopsy is CK5/14 positive and involucrin negative;

(b) determining the nuclear localization of Bmi1;

(c) quantitating the number of CD44 positive, lineage marker negative cancer cells; and (d) identifying cancer stem cells as CD44 positive, lineage marker negative cancer cells of head and throat squamous carcinoma, wherein said stem cells are present in histological microdomains.

* * * * *